(12) United States Patent
Kumar et al.

(10) Patent No.: US 11,510,960 B2
(45) Date of Patent: Nov. 29, 2022

(54) BIOFILM DISRUPTING COMPOSITION FOR USE ON CHRONIC WOUNDS

(71) Applicants: Whiteley Corporation Pty Ltd, North Sydney (AU); The University of Sydney, The University of Sydney (AU)

(72) Inventors: Theerthankar Das Ashish Kumar, Kensington (AU); Jim Manos, Oatley (AU); Gregory Stuart Whiteley, Queenscliff (AU); Trevor Owen Glasbey, Tanilba Bay (AU)

(73) Assignees: Whiteley Corporation PTY LTD, North Sydney (AU); The University of Sydney, New South Wales (AU)

( * ) Notice: Subject to any disclaimer, the term of this patent is extended or adjusted under 35 U.S.C. 154(b) by 357 days.

(21) Appl. No.: 16/470,904

(22) PCT Filed: Dec. 21, 2017

(86) PCT No.: PCT/AU2017/051438
§ 371 (c)(1),
(2) Date: Jun. 18, 2019

(87) PCT Pub. No.: WO2018/112544
PCT Pub. Date: Jun. 28, 2018

(65) Prior Publication Data
US 2020/0085919 A1    Mar. 19, 2020

(30) Foreign Application Priority Data
Dec. 22, 2016 (AU) ................................ 2016905326

(51) Int. Cl.
*A61K 36/31* (2006.01)
*A61K 38/06* (2006.01)
(Continued)

(52) U.S. Cl.
CPC .......... *A61K 38/063* (2013.01); *A61K 31/496* (2013.01); *A61K 31/7036* (2013.01);
(Continued)

(58) Field of Classification Search
CPC ..................................................... A61K 36/31
See application file for complete search history.

(56) References Cited

U.S. PATENT DOCUMENTS

2006/0162722 A1 *  7/2006  Boehm ............. A61M 16/0006
                                                              128/200.14
2008/0139545 A1     6/2008  Choe et al.

FOREIGN PATENT DOCUMENTS

| IL | WO0209636 A2 * | 2/2002 |
| WO | 1993021958 A1 | 11/1993 |
| WO | 2011097347 A2 | 8/2011 |

OTHER PUBLICATIONS

International Preliminary Report on Patentability in PCT/AU2017/051438 (dated Apr. 15, 2019).
(Continued)

*Primary Examiner* — Rosanne Kosson
(74) *Attorney, Agent, or Firm* — Andrew S. Langsam; Joseph Micali (57) ABSTRACT

A biofilm disrupting composition for use on chronic wounds comprising (i) at least one biologically acceptable thiol based antioxidant (ii) at least one biofilm disruptor and (iii) at least one biocide. Also disclosed is a process of preparing the composition. Also disclosed is the use of the composition for the manufacture of a medicament for the treatment of a chronic wound, and a method of treating a chronic wound in a patient comprising administering the biofilm disrupting composition.

18 Claims, 1 Drawing Sheet

(51) Int. Cl.
*A61P 31/04* (2006.01)
*A61K 31/496* (2006.01)
*A61K 31/7036* (2006.01)
*A61K 38/46* (2006.01)
*A61K 33/18* (2006.01)
*A61K 33/30* (2006.01)
*A61K 47/38* (2006.01)
*A61K 9/00* (2006.01)
*A61K 9/06* (2006.01)

(52) U.S. Cl.
CPC .............. *A61K 33/18* (2013.01); *A61K 33/30* (2013.01); *A61K 38/465* (2013.01); *A61K 47/38* (2013.01); *A61P 31/04* (2018.01); *C12Y 301/21001* (2013.01); *A61K 9/0014* (2013.01); *A61K 9/06* (2013.01)

(56) References Cited

OTHER PUBLICATIONS

Klare, W et al (2016) 'Glutathione-Disrupted Biofilms of Clinical Pseudomonas aeruginosa Strains Exhibit an Enhanced Antibiotic Effect and a Novel Biofilm Transcriptome' Antimicrobial Agents and Chemotherapy 60:4539-4551.

Tetz et al., "Effect of DNase and Antibiotics on Biofilm Characteristics," Antimicrobial Agents and Chemotherapy, 53 (3):1204-1209 (Mar. 2009).

* cited by examiner

Figure 1                    Figure 2

BIOFILM DISRUPTING COMPOSITION FOR USE ON CHRONIC WOUNDS

FIELD OF THE INVENTION

The invention relates to a biofilm disrupting composition. The composition is useful for the disruption and/or removal of bacterial biofilms from a range of surfaces including living tissue, medical devices and environmental surfaces. In particular, the invention may be used to disrupt biofilm found on chronic wounds such as diabetic foot ulcers. The invention is also efficacious for the treatment of burns colonized with biofilm forming organisms.

BACKGROUND OF INVENTION

A biofilm is any group of microorganisms in which cells stick to each other and often these cells adhere to a surface. These adherent cells are frequently embedded within a self-produced matrix of extracellular polymeric substance (EPS). The biofilm EPS is typically comprised of a polymeric conglomeration generally composed of extracellular DNA, proteins, and polysaccharides. Biofilms may form on living or non-living surfaces and can be prevalent in natural, industrial and hospital settings. The microbial cells growing in a biofilm are physiologically distinct from planktonic cells of the same organism, which, by contrast, are single-cells that may float or swim in a liquid medium.

Microbes form a biofilm in response to many factors, which may include cellular recognition of specific or non-specific attachment sites on a surface, nutritional cues, or in some cases, by exposure of planktonic cells to sub-inhibitory concentrations of antibiotics. When a cell switches to the biofilm mode of growth, it undergoes a phenotypic shift in behavior in which large suites of genes are differentially regulated.

ESKAPE organisms are a group of clinically relevant multi-drug resistant organisms. These are *Enterococcus faecium, Staphylococcus aureus, Klebsiella pneumoniae, Acinetobacter baumannii, Pseudomonas aeruginosa* and *Enterobacter* spp, all of which are capable of forming biofilm, and also capable of serious infections in hospitals, particularly in ICU's.

Bacterial Biofilm and Chronic Infections

Many chronic infections are associated with biofilm infections. Some examples of these are:

Chronic Rhinosinusitis

Rhinosinusitis is one of the most common medical complaints in the United States, affecting up to 16% of the population. It is associated with over 13 million physician visits per year and an estimated aggregated cost of over $6 billion annually. Patients with chronic rhinosinusitis (CRS) demonstrate worse quality-of-life scores than those suffering from chronic obstructive pulmonary disease, congestive heart failure, back pain, or angina. Despite the large societal impact and economic burden, the pathophysiology of CRS remains largely unsolved. One possible mechanism for the chronic nature of this disease is the involvement of bacterial biofilms, which represent a phenotypic change in bacteria that make them resistant to conventional treatment strategies. The role of bacterial biofilms in CRS has been reviewed by Suh et al ("Biofilms in chronic rhinosinusitis", *Curr Opin Otolaryndol Head Neck Surd*. (2010) 18, 27-31).

Chronic Otitis Media

Characterized as either an acute or chronic disease, otitis media (OM) is the most common illness for which children visit a physician, receive antibiotics or undergo surgery in the United States. There are two subtypes of chronic OM: recurrent OM (ROM) is diagnosed when children suffer repeated infections over a span of time and during which clinical evidence of the disease resolves between episodes, and chronic OM with effusion is diagnosed when children have persistent fluid in the ears that lasts for months in the absence of any other symptoms except conductive hearing loss.

Though antibiotics have proven to be effective for children with acute OM where biofilms have not yet formed, those with chronic disease typically benefit little from the drugs and more so from myringotomy, a surgical procedure in which small tubes are placed in the eardrum to continuously drain infectious fluid (called effusion).

In a study by Hall-Stoodley et al ("Direct Detection of Bacterial Biofilms on the Middle-Ear Mucosa of Children With Chronic Otitis Media", JAMA, (2006), 296, 202-211), the involvement of biofilm was directly demonstrated on a range of patients.

Of the 26 children undergoing tympanostomy tube placement, 13 (50%) had OM with Effusion (OME), 20 (77%) had recurrent OM, and 7 (27%) had both diagnoses; 27 of 52 (52%) of the ears had effusions, 24 of 24 effusions were polymerase chain reaction (PCR)-positive for at least 1 OM pathogen, and 6 (22%) of 27 effusions were culture-positive for any pathogen.

Mucosal biofilms were visualized by Confocal laser scanning microscopy on 46 (92%) of 50 middle ear mucosal (MEM) specimens from children with OME and recurrent OM using generic and pathogen-specific probes. Biofilms were not observed on 8 control MEM specimens obtained from the patients undergoing cochlear implantation.

Of the identified organisms found were *Streptococcus pneumoniae, Haemophilus influenza*, and *Moraxella catarrhalis*.

Catheter Associated Urinary Tract Infections (CAUTI)

A urinary tract infection (UTI) is an infection involving any part of the urinary system, including urethra, bladder, ureters, and kidney. UTIs are the most common type of healthcare-associated infection reported to the National Healthcare Safety Network (NHSN). Among UTIs acquired in the hospital, approximately 75% are associated with a urinary catheter, which is a tube inserted into the bladder through the urethra to drain urine. Between 15-25% of hospitalized patients receive urinary catheters during their hospital stay. The most important risk factor for developing a catheter-associated UTI (CAUTI) is prolonged use of the urinary catheter. Therefore, catheters should only be used for appropriate indications and should be removed as soon as they are no longer needed.

The pathogenesis of CAUTI is related to the susceptibility of inert catheter material to microbial colonization. On the surface of normal bladder mucosa, binding of bacteria triggers an inflammatory response that results in an influx of neutrophils and sloughing of epithelial cells with bound bacteria. Both processes contribute to clearance of the bacteria from the mucosal surface. In contrast, catheter surfaces have no inherent defense mechanisms. The first step in biofilm formation on a urinary catheter is deposition of a conditioning film of host urinary components, including proteins, electrolytes, and other organic molecules. This conditioning film can transform the surface of the urinary catheter and neutralize any antiadhesive properties. Free-swimming bacteria attach to the surface through hydrophobic and electrostatic interactions and through the use of flagella. Attachment is followed by cell division, recruitment of additional planktonic bacteria, and secretion of extracellular matrix. Cell-to-cell signaling directs the formation of loosely packed 3-dimensional structures with fluid channels between them to permit exchange of nutrients and wastes. Detachment of individual organisms from the biofilm completes the cycle and can also seed the urine with pathogens.

The reason that biofilm is so prevalent on urinary catheters is that it conveys a survival advantage to the microorganisms; for this same reason, urinary catheter biofilm is difficult to eradicate. Organisms in a biofilm function as a community and communicate closely with one another. Survival advantages conferred by the biofilm community include resistance to being swept away by simple shear forces, resistance to phagocytosis, and resistance to antimicrobial agents.

Not only does the urinary catheter invite biofilm formation, but the presence of the catheter itself impairs many of the normal defense mechanisms of the bladder. The urinary catheter connects the heavily colonized perineum with the normally sterile bladder, and it provides a route for bacterial entry along both its external and internal surfaces. Urine often pools in the bladder or in the catheter itself, and urinary stasis encourages bacterial multiplication. Obstruction of the catheter can lead to overdistension and ischemic damage of the bladder mucosa, thus, increasing its susceptibility to bacterial invasion. The catheter also damages the bladder mucosa by triggering an inflammatory response and by mechanical erosion.

Once organisms gain access to the catheterized urinary tract, low-level bacteriuria usually progresses to >$10^5$ colony-forming units/mL within 24 to 48 hours in the absence of antimicrobial therapy. For patients with an indwelling urethral catheter, the daily rate of acquisition of bacteriuria is 3% to 10%.

A study of 20 patients who were chronically catheterized found that 98% of 605 consecutive weekly urine specimens contained >$10^5$ bacteria/mL of urine, and 77% of the urine specimens contained multiple species. Monthly urine cultures for patients with long-term indwelling catheters show that the bacterial flora is constantly shifting and changing, regardless of antibiotic use (see BW Trautner and RO Darouiche, "Role of biofilm in catheter-associated urinary tract infection", Am. J. Infect. Control, (2004), 32, 177-183.

Chronic Wounds

Diabetic foot ulcer is a major complication of diabetes mellitus, and probably the major component of the diabetic foot.

Wound healing is an innate mechanism of action that works reliably most of the time. A key feature of wound healing is stepwise repair of lost extracellular matrix (ECM) that forms the largest component of the dermal skin layer. In some cases however, certain disorders or physiological insult disturbs the wound healing process. Diabetes mellitus is one such metabolic disorder that impedes the normal steps of the wound healing process. Many studies show a prolonged inflammatory phase in diabetic wounds, which causes a delay in the formation of mature granulation tissue and a parallel reduction in wound tensile strength.

Treatment of diabetic foot ulcers typically will include: blood sugar control, removal of dead tissue from the wound (debridement), wound dressings, and removing pressure from the wound through techniques such as total contact casting. Surgery in some cases may improve outcomes. Hyperbaric oxygen therapy may also help but is expensive.

It occurs in 15% of people with diabetes, and precedes 84% of all diabetes-related lower-leg amputations. 4% of all diabetic patients will undergo an amputation during their lifetime in no small part due to non-healing ulcerative wounds.

An additional complication of chronic wounds such as diabetic foot ulcers is the wound bed often becomes infected and colonised with various biofilm forming opportunistic pathogens, often leading to the formation of a biofilm. Whilst a single bacterial species may commence construction of a biofilm on a wound, other species are likely to be involved, even where a single species may dominate the biofilm matrix. One consequence of this biofilm colonisation is one sees a different clinical pattern of infections that are persistent, they wax and wane and respond incompletely to appropriate antibiotics, only to re-emerge once the antibiotics are withdrawn. Chronic wounds, with their persistence, undulant inflammation and incomplete response to antibiotics and topical biocides seem as if they could be related to other chronic infections.

The literature about common chronic infections associated with biofilm demonstrates that clinical cultures are ineffective in identifying the associated bacteria. In response, DNA diagnostic methods were developed to exploit the strengths of different molecular testing methods, which included quantitative polymerase chain reaction (PCR) and sequencing technologies. These DNA-based technologies were able to identify and quantify the microorganisms present in chronic wounds, as well as in other chronic infections.

One consistent finding in most chronic wounds is that there are high numbers of multiple species present in a very small area on the wound surface (see for example Gjødsbøl et al, "Multiple bacterial species reside in chronic wounds: a longitudinal study", International Wound Journal, 2006, 3, 225-231, and Dowd et al, "Survey of bacterial diversity in chronic wounds using Pyrosequencing, DGGE, and full ribosome shotgun sequencing", BMC Microbiology, 2008, 8, 43).

Since bacteria growing in planktonic phenotype compete, this finding is strong evidence that the bacteria on the surface of chronic wounds are biofilm phenotype. Biofilm is known for its cooperative diversity. The diversity identified by molecular methods along with imaging has established that biofilm is present on the surface of chronic wounds. DNA-based methods also identify with far greater accuracy and comprehensiveness than clinical cultures, the microorganisms interfering with the healing of chronic wounds.

By using these diagnostic tools, biofilm-based wound care has been able to produce statistically significant improvements in wound outcomes. The improvement in identification of the microorganisms allows for a more appropriate use of commercially available systemic antibiotics and topical antimicrobial products. The reduction in the use of first-line methicillin-resistant Staphylococcus aureus (MRSA) antibiotics wound care has been dramatic.

One risk arising from bacterial proliferation within a biofilm coated wound is that of practical species dominance. Some bacteria such as *Pseudomonas aeruginosa* release cytotoxic molecules such as pyocyanin into the surrounding media or biofilm which either destroys or dissuades the competitive proliferation of other species. Both Gram Negative and Gram Positive bacteria have the capacity to release toxigenic molecules into tissues and fluids surrounding a colonised site of infection. A side effect of this release of bacterial toxins is the effect on underlying skin or bodily tissue, which is similarly destroyed or disrupted. Thus the bodily defences to neutralise the bacteria such as immunological secretions are neutralised and overwhelmed by the presence of the antigenic molecules released in the biofilm.

It has become clear that, if targeted treatments could be developed specifically for the microorganisms identified on the surface of chronic wounds, wound care outcomes could be improved.

A typical treatment option for a chronic foot ulcer is debridement of the wound. Whilst sometimes, debridement occurs naturally on its own thanks to the body's own ability to shed off dead tissue, more often, it requires a medical procedure. There are two different categories of debridement: active and autolytic. Autolytic debridement involves application of hydrocolloids and hydrogels to enhance moisture in the affected area in order to degrade it so the body will naturally de-slough the dead tissue. Active debridement involves the manual removal of necrotic material, and it comes in several types of procedures, such as:

Surgical debridement: During this operation, a clinician will completely remove the necrotic material using a scalpel and forceps, resulting in a bleeding wound bed.

Sharp debridement: This is similar to surgical debridement, except that it involves the use of surgical scissors.

Larval therapy: Maggots or their larvae are placed on the wound site and eat away at the dead skin, leaving the healthy tissue behind.

Clinicians largely agree that the removal of devitalised tissue improves wound healing, a concept that is accepted by Center for Medicare Services (CMS) Fiscal Intermediaries, through Local Coverage Decisions. However, at molecular and cellular levels, there is little evidence to show how debridement exerts a positive effect on wound healing.

Work conducted by Wolcott et al ("Biofilm maturity studies indicate sharp debridement opens a time-dependent therapeutic window"; Journal of Wound Care (2010) 19, 320-328) has demonstrated that bacteria in all of the various stages of biofilm phenotype tightly adhere to the surfaces of chronic wounds. Although they have been shown to organise around blood vessels and extend into the host in acute wounds, the majority of chronic wound biofilms seen under scanning electron microscopy and light microscopy appear to reside on the extracellular matrix of the wound bed itself. Because it accumulates and becomes established quickly it is unclear what beneficial effects (if any) removing the biofilm may have on wound healing.

Biofilms are well documented, both generally and in their development stages. Typically, planktonic bacteria undergo a phenotypic metamorphosis through attachment to a surface, that leads to microcolony formation (where they are metabolically more active) and then progress into mature biofilms with a protective matrix.

Formation of a mature biofilm is also associated with a slowing down of the metabolic rate of the bacteria within the biofilm. The formation of the protective matrix of EPS, along with the slowed metabolism results in the constituent micro-organisms being less susceptible to antimicrobials and other biocides. It follows therefore that any procedure that disrupts the biofilm such as sharp debridement may create a "window of opportunity" by removing the bulk of the mature biofilm. The metabolic rate of the residual microorganisms are forced to increase as the biofilm grows back and re-establishes itself.

In a study on three patients with non-healing venous leg ulcers, one week after debridement the patients' bioburden was removed via sharp debridement and the sample was evaluated for the ability of gentamicin to kill bacteria within the biofilm. It was shown that there was an average 4 log reduction in bacteria after antibiotic treatment of the mature (pre-study) biofilm. At baseline, the three VLU's chosen for the study all had significant and high levels of $P.$ $aeruginosa$ (average $5.2 \times 10^8$ CFU/5 mg bioburden). After initial debridement the bacterial populations rapidly grew back to the original concentrations. However, at 24 hours post-debridement all of the biofilms were more susceptible to antibiotic treatment showing greater than a nine-fold reduction in concentration in relation to the control biofilm and a significant difference was observed between the susceptibility of day 0 pre-debridement and day 1 (24 hours) post-debridement.

Burn Infections

Another similar area where biofilm formation can adversely impact the healing process is burns. The survival rates for burn patients have improved substantially in the past few decades due to advances in modern medical care in specialised burns centres. Improved outcomes have been attributed to medical advances in fluid resuscitation, nutritional support, pulmonary care, burns wound care and infection control practices. Burns are one of the most common devastating forms of trauma. Burn patients are ideal hosts for opportunistic infections for a variety of reasons.

Firstly, thermal injury causes instant coagulative necrosis, which rapidly becomes a favourable niche for bacterial colonisation and proliferation. The eschar provides a devitalised, protein rich environment, which further benefits bacterial proliferation through its exclusion from the systemic circulation and impaired local immune responses. The burn site remains relatively sterile during the first 24 hour; thereafter, colonization of the wound by gram negative bacteria is common.

Secondly, organisms originate from the patient's own skin, gut and respiratory flora, as well as from contact with contaminated health care environments and workers may also colonise the wound site, again leading to biofilm formation.

Skin commensals are involved in biofilm formation around inserted medical devices (see for example Deva et al, "The Role of Bacterial Biofilms in Device-Associated Infection", Plastic and Reconstructive Surgery Journal, (2013), 132, 1319-1328) and are a ubiquitous presence and risk with unresolved or open wounds.

Thirdly, once formed, biofilms act as efficient barriers against antimicrobial agents and the host immune system, resulting in persistent colonization and/or infection at the site of biofilm formation. Also, bacteria within a biofilm typically undergo a phenotypic change whereby microbial virulence factor production is altered and metabolic rate and motility are reduced.

In a study by Yarets ("Effective biofilm removal and changes in bacterial biofilm building capacity after wound debridement with low-frequency ultrasound as part of wound bed preparation before skin grafting"; Chronic Wound Care Management and Research; (2017), 4, 55-64), the benefits of addressing wound biofilm in patients suffering chronic wounds was demonstrated. Treated wounds included traumatic ulcers as a result of mechanical or thermal trauma (n=49), pressure sores (n=14), venous leg ulcers (n=32), and inflammatory ulcers, which derived from necrotizing infections of soft tissue or from surgical site infections (n=45). From 140 patients enrolled, 86 were males and 54 females. Patient age ranged from 19 to 79 years. The duration of wounds was 28-365 days.

In this study, it was demonstrated that patients exposed to the usual protocol in which, after initial wound cleansing with saline solution, patients received 7-14 days of wound therapy following the local treatment protocol of the hospital. Treatment measures included the use of antiseptic bandages, chlorhexidine, povidone iodine, and polyethylene glycol-based ointments. Following initial wound therapy, patients underwent one UAW session as a wound bed preparation measure before surgical wound closure and skin grafting. Despite <$10^4$ CFU/mL bacteria detected at wound site shortly before grafting wounds of patients subjected to a single UAW round, complete graft healing was observed in 75% of cases (30/40) and complications within the immediate post-procedural period in 25% cases (10/40).

However, in a revised protocol, after patient's admission, all wounds were cleaned with saline solution and then treated for 1-3 days according to the local treatment protocol of the hospital. Then the first UAW procedure was conducted followed by local wound treatment for 7-14 days according to the local treatment protocol. After 7-14 days of dressing treatment, the second UAW procedure was conducted shortly before surgical wound closure with skin grafting. Patients were found to have between $10^1$-$10^2$ CFU/mL bacteria detected at wound site shortly before skin grafting, complete graft take was observed within 1-3 days and complete graft healing after 7-9 days with no complications being observed in all 47 patients.

It is hypothesised therefore that if the biofilm colonising the wound bed of a chronic wound, or burn could be disrupted without resort to surgical intervention or similar traumatic treatments, more favoured patient outcomes may be achieved, without recourse to traumatic treatment options such as sharp debridement.

Inhaled glutathione (GSH) therapy has been used to reduce oxidative stress in cystic fibrosis patients and inhibit proliferation of *Pseudomonas* infections in cystic fibrosis patients, including increasing susceptibility of the *Pseudomonas* to antibiotics (*Zhang and Duan*, 2009 and NCT01450267). It has also been found that GSH and DNase 1 can be combined for treating chronic *Pseudomonas* infections in individuals with cystic fibrosis (Klare et al., Canberra ASM meeting, July 2015). Further, GSH and DNase 1 have been found to be useful in the disruption of *Pseudomonas* biofilms in cystic fibrosis-like media and increasing susceptibility of the *Pseudomonas aeruginosa* to antibiotics (Klare et al., 2016 *Antimicrobial Agents and Chemotherapy* 60 (8) 4539-4551)).

Surprisingly it has been found that the application of this combination therapy to chronic wounds, such diabetic foot ulcers, burns and chronically infected surgical wounds also responds favourably to this combination therapy.

It would be desirable to provide a composition which is effective against biofilms and in particular biofilms caused by ESKAPE organisms.

A reference herein to a patent document or other matter which is given as prior art is not to be taken as an admission that that document or matter was known or that the information it contains was part of the common general knowledge as at the priority date of any of the claims.

SUMMARY OF THE INVENTION

It has been surprisingly found that a composition comprising a combination of a redox based viscosity modifier, a biofilm disrupter and a biocide provides enhanced biofilm disruption. The biofilm disrupting composition described herein has been found to be effective against biofilms caused by ESKAPE organisms. More specifically, the composition of the invention has been found effective against biofilms caused by ESCAPE organisms colonizing external wounds resulting from chronic disease (for example diabetes) or traumatic events such as burns.

Disclosed herein is provided a biofilm disrupting composition comprising:
(i) at least one redox based viscosity modifier;
(ii) at least one biofilm disruptor; and
(iii) at least one biocide.

More specifically, according to a first embodiment of the invention there is provided a biofilm disrupting composition for use on chronic wounds comprising:
(i) at least one biologically acceptable thiol based antioxidant;
(ii) at least one biofilm disruptor; and
(iii) at least one biocide.

According to a second embodiment of the invention there is provided a biofilm disrupting composition when used for treatment of chronic wounds comprising:
(i) at least one biologically acceptable thiol based antioxidant;
(ii) at least one biofilm disruptor; and
(iii) at least one biocide.

The composition of the invention may be in the form of an aqueous solution intended to perfuse the wound.

The composition of the invention may be in the form of a gel intended to coat the wound bed.

According to a third embodiment of the invention there is provided a process of preparing a biofilm disrupting composition of the first or second embodiments which process comprises combining at least one biologically acceptable thiol based antioxidant, at least one biofilm disruptor and at least one biocide, to form said composition.

According to a fourth embodiment of the invention there is provided the use of a composition comprising at least one biologically acceptable thiol based antioxidant, at least one biofilm disruptor and at least one biocide, for the manufacture of a medicament for the treatment of a chronic wound.

According to a fifth embodiment of the invention there is provided the use of composition of the first or second embodiments for the manufacture of a medicament for the treatment of a chronic wound.

According to a sixth embodiment of the invention there is provided a method of treating a chronic wound in a patient, comprising administering to said wound a biofilm disrupting composition according to first or second embodiments in an amount which effectively treats said wound.

Throughout the description and claims of the specification, the word "comprise" and variations of the word, such as "comprising" and "comprises", is not intended to exclude other additives, components, integers or steps.

The ingredients of the composition of the invention act synergistically providing superior biofilm disruption. Without wishing to be bound by theory, it is believed that the redox based viscosity modifier, by virtue of its low molecular weight and therefore high diffusivity, reduces the viscosity of the biofilm, thus facilitating the diffusion in of the biofilm disruptor enzymes, allowing greater access to the biopolymer chains, leading to more efficient scission. Finally, with the biofilm EPS degraded, the biocide will have greater access to the microbial species.

DETAILED DESCRIPTION OF THE INVENTION

Biologically Acceptable Thiol Based Antioxidant

The biofilm disruptor compositions disclosed herein comprise at least one redox based viscosity modifier. In particular, the composition of the invention comprises at least one biologically acceptable thiol based antioxidant. This is a biologically and pharmaceutically acceptable compound containing a sulfhydryl group (also known as a thiol group) capable of reducing disulphide bonds and therefore is capable of disrupting disulphide cross-links found within the extracellular polysaccharide typically found in most biofilms. Typically, such compounds will have a redox potential in the range of −0.05V to −0.50V.

Examples of suitable biologically acceptable thiol based antioxidants include mercaptoethanol, N-acetyl cysteine (NAC), glutathione (GSH), thiamphenicol glycinate acetylcysteinate (TGA), sodium mercaptoethane sulfonate, dithiothreitol (DTT), dithiobutylamine and other similar compounds. Other examples of suitable redox based viscosity modifiers are compounds such as lipoic acid or erdosteine, which are capable of generating free thiol groups in vivo following first pass metabolism.

In a preferred embodiment the biologically acceptable thiol based antioxidant is glutathione (GSH).

Biofilm Disruptor

The biofilm disruptor is an agent that can either lead to scission of the biopolymers that make up the biofilm, or lead to a disruption of the adhesive forces that help attach the biofilm to its supporting surfaces. The biofilm disruptor breaks down the polymeric components of the EPS of bacterial biofilm into smaller, more diffusible components. The redox based viscosity modifier in the composition of the invention is believed to act synergistically with the biofilm disruptor by reducing the cross-linking between the various EPS biopolymers, and thus lowering the viscosity of the biofilm, so allowing the biofilm disruptor to more readily diffuse into their substrate biopolymers, and also allowing the more ready outward diffusion of the resultant biopolymer fragments following enzyme degradation.

The biofilm disruptor may be at least one enzyme selected from the group consisting of protease, amylase, cellulase, and DNase. Preferably one or more of the enzymes is DNase. More preferably, the composition of the invention will contain two or more of these enzyme types.

Given that the tertiary structure of most of the enzymes used in the composition of the invention is globular, the diffusion of the enzyme molecule into its substrate is likely to be limited by the high viscosity likely to be encountered in the biofilm EPS. When the enzyme in the composition of the invention is DNase, it is believed that it degrades the extracellular chains of DNA and other nucleic acids released into the extracellular matrix by the lysis of bacterial cells, thus releasing the cell genetic material into the EPS. Other DNA packages, such as plasmids, which are small circular sections of double stranded DNA found separate from chromosomal DNA within most bacterial species may also be released and taken up by live bacteria within the biofilm, thus providing a mechanism for the exchange of genetic information such as antibiotic resistance. It is believed that, by using DNase into the composition of the invention, this may serve to restrict further genetic exchange.

Other examples of a biofilm disruptor which may be used in the biofilm disrupting compositions disclosed herein may comprise a blend of surfactants and/or solvents which preferably lower the surface tension of the composition to at least 35 mN/m. Preferably, the surfactants are non-toxic and non-irritating at the in-use concentration. The surfactants may be selected from the group consisting of anionic, cationic, zwitterionic or non-ionic surfactant types, or compatible mixtures thereof.

A cationic surfactant may also function as a biocide. Examples of biocidal cationic surfactants which may be used in the biofilm disrupting compositions disclosed herein include benzalkonium chloride, benzethonium chloride, dimethyl didecylammonium chloride etc. It is recognized that cationic surfactants will typically be incompatible with anionic surfactants, and therefore mixtures of surfactants containing cationic surfactants will not contain anionic surfactants and vice versa.

Preferred are mixtures of non-ionic surfactants such as alkyl polyglucosides, alcohol ethoxylates, polyethylene glycol/polypropylene glycol block copolymers (Pluronics™), N-alkyl pyrrolidinones (e.g. Surfadone™)

Representative examples of surfactants in the biofilm disrupting compositions disclosed herein may be found in U.S. Pat. No. 6,855,678, incorporated herein in its entirety by way of reference. More specifically, the surfactant may be selected from the group consisting of an alkyl polysaccharide surfactant, a nonionic surfactant, an alkyl, aryl or amine halide surfactant, a polyethoxylate of an alkylamine surfactant, and a lauric mono, di- or triethanolamine. More preferably, said nonionic surfactant may be selected from the group consisting of a nonionic surfactant containing from 8 to 18 carbon atoms and/or from 6 to 12 moles of ethyleneoxide; an amine oxide containing from 12 to 18 carbon atoms; an ethoxylate alkyl amine containing from 10 to 14 carbon atoms and 1 to 6 moles of ethylene oxide; an alkyl (C8-12) dimethyl benzyl amine halide; and a lauric mono, di- or triethanolamine.

Other surfactants which may be used in the biofilm disrupting compositions disclosed herein are natural biosurfactants which may play an important role in natural wound healing. Examples may include biosurfactants isolated from *Bacillus stratosphericus* sp. A15 using Catla catla fish fat (Sana et al, "Towards the development of an effective in vivo wound healing agent from *Bacillus* sp. derived biosurfactant using Catla catla fish fat", RSC Adv. (2017, 7, 13668-13677), and/or lipopeptide microbial surfactants such as *Bacillus subtilis* SPB1 lipopeptide biosurfactant (see for example Zouari et al, "Evaluation of dermal wound healing and in vitro antioxidant efficiency of *Bacillus subtilis* SPB1 biosurfactant", Biomedicine & Pharmacotherapy (2016), 84, 878-891)

Solvents which act as a biofilm disruptor, which may be used in the biofilm disrupting compositions disclosed herein, are preferably selected from the group consisting of one or more low molecular weight polar water soluble solvents selected from the group consisting of primary or secondary alcohols; glycols; esters; ketones; aromatic alcohols; and cyclic nitrogen solvents containing 8 or less carbon atoms. More preferably, the one or more solvent is selected from the group consisting of a (C1-6) alcohol; ester; ether; ketone; glycol; or their methyl and ethyl esters and ethers; an aromatic alcohol containing 8 or less carbon atoms; pyrrolidone; and methyl pyrrolidone.

The surfactant and/or solvent have the added advantage of providing a composition with improved surface wetting characteristics. In a more preferred embodiment, the biofilm disrupting composition will comprise one or more surfactants/solvents providing a surface tension of the solution of less than 40 nN/m. In an even more preferred embodiment, the surfactant/solvent(s) will be selected in order to reduce the surface tension of the composition to below 30 nN/m.

Without wishing to be bound by theory, it is believed that solutions with a very low surface tension (i.e. 35 nN/m or less) can penetrate between the biofilms basal layer and the substrate on which the biofilm has grown thus leading to detachment of the biofilm from the surface. This can lead to clumps of biofilm detaching from the surface, thus being available from attack from both anterior and posterior surfaces.

Biocide

The biofilm disrupting composition comprises at least one biocide. The biocide may be selected from an antibiotic or a disinfectant, depending on the intended use of the composition. In the present invention the biocide is selected from the group consisting of an antibiotic and an antiseptic.

In the case of a composition intended for the in-vivo removal of a biofilm, such as that found in the lungs in cystic fibrosis patients, the biocide will be a pharmacologically acceptable antibiotic preferably selected from the group consisting of ciprofloxacin, dexamethasone, amoxicillin/clavulanate, cefixime, cefaclor, clarithromycin, levofloxacin, moxifloxacin and telithromycin.

In the case of compositions intended for the treatment of chronic wounds such as diabetic foot ulcers, burns, infected surgical wounds etc, the biocide may be comprised of a topical antibiotic such as (but not limited to) sulfacetamide sodium, erythromycin, silver sulfadiazine, mupirocin, bacitracin, neomycin, polymyxin, bacitracin, neomycin, polymyxin B, and pramoxine.

The biocide may also comprise of an antiseptic species such as cadexomer iodine, povidone iodine, cetrimide, benzalkonium chloride, chlorhexidine gluconate, polyhexanide, hydrogen peroxide, octenidine dihydrochloride, diamidines, silver compounds, zinc salts, etc.

The function of the biocide is to kill the organisms responsible for the formation of the biofilm. This will have the secondary effect of removing the propensity of the biofilm to release infectious agents that often lead to chronic illnesses with in-vivo biofilms, or indeed serve as an environmental reservoir of infectious organisms The at least one biologically acceptable thiol based antioxidant and the at least one biofilm disruptor within the composition of the invention act synergistically with the biocide. Typically, microorganisms found within biofilms will show a high level of resistance to biocidal agents, predominantly due to the fact that microorganisms are embedded deep within the EPS and thus shielded from biocides. A second factor for the resistance of the organisms to biocidal compounds is the fact that many organisms within the biofilm may exchange genetic information, such as resistance to antimicrobial species.

Ancillary Agents

The biofilm disrupting composition may optionally contain other ingredients such as secondary surfactants, tonicity modifiers, pH buffers, thickening agents, colourants, preservatives and perfumes.

Tonicity Modifying Agent

The biofilm disrupting composition may also contain tonicity modifying ingredients. These may comprise inorganic salts, for example sodium bromide, potassium bromide, sodium chloride, potassium chloride, sodium acetate, potassium acetate, sodium citrate, potassium citrate, sodium phosphate, potassium phosphate, or may comprise organic tonicity modifiers such as propylene glycol, glycerol, mannitol, arabitol, glucose, fructose etc. The biofilm disrupting composition may be isotonic (i.e. 250-350 mOsmal/Kg) or hypotonic (i.e. <250 mOsmal/Kg). Preferably the biofilm disrupting composition will not be hypertonic as this may lead to dehydration of the biofilm, resulting in a reduced tendency of the composition to diffuse into the biofilm and attack it.

Colouring Agent

The biofilm disrupting composition may also comprise colouring agents. The colouring agents may be added to provide a function to the composition, such as the staining of components found within the bacterial biofilm, or may just be added to provide an aesthetically pleasing solution.

When the colouring agent is added to stain components of the biofilm, the resultant staining may provide a visual cue as to the presence of the biofilm, thus also provide a means of monitoring its removal. Suitable colouring agents capable of staining biofilm components (for example protein, polysaccharide or bacterial cell walls) will include Coomassie Brilliant Blue, Crystal Violet, erythrosine and tartrazine.

Thickening Agents

The biofilm disrupting composition may also be in the form of a gel, thus allowing the composition to remain in prolonged contact with the biofilm contaminated surface. The gel may exhibit Newtonian behavior, or non-Newtonian behavior. Various thickening agents may be incorporated into the composition to modify its viscosity. For example, incorporation of the sodium salt of a cross-linked polyacrylate (for example Carbomers) will lead to the formation of a non-Newtonian sheer thinning gel. Similarly, other viscosity modifying agents such as hyaluronic acid, may be used. These anionic thickening agents are however susceptible to the ionic strength of the composition, and thus work less efficiently in the presence of electrolytes. Thickening agents that are substantially unaffected by the presence of electrolytes are polysaccharide derivatives such as hydroxyethyl cellulose, guar, hydroxyethyl guar, xanthan gum etc.

Highly preferred thickening agents would be methyl cellulose, or hydroxypropyl methyl cellulose which can exhibit a reversible thermal gelation. As is widely known in the art, the thermal gelation temperature may be modified by the addition of salts, or non-electrolytes such as sorbitol, sucrose, glucose etc. Such systems are described in "Methocel Cellulose Ethers Technical Handbook"; Dow Chemicals, September 2002, incorporated herein as a reference document. In a highly preferred embodiment, a methyl cellulose containing composition with a gelation temperature between 30 and 35° C. is contemplated.

The temperature at which the thermally reversible gelation of the hydroxypropyl methyl cellulose or the methyl cellulose thickened formulations occurs may be modified by the addition of various solutes. Most electrolytes, as well as sucrose, glycerine, etc., lower the gel point because they have a greater affinity for water and dehydrate the cellulosic polymer. Decreases in gel temperature are a function of the ions present in the additive. Examples of solutes known to lower the temperature of gelation (thermal gelation temperature lowering agents) may be selected from one or more of the following, sodium chloride, magnesium chloride, iron III chloride, sodium sulfate, aluminium sulfate, sodium carbonate, sodium bicarbonate, sodium citrate, Sorbitol, glycerine, trimethylglycine, glucose, maltose, fructose.

Materials known to increase the gelation temperature include: polyethylene glycol 400, polyethylene glycol 800, and polypropylene glycol. Typically, the increase in the thermal gel point is directly proportional to the increase in concentration of 15 the additive.

The temperature of gelation can also be controlled by the concentration of the hydroxypropyl methyl cellulose or the methyl cellulose thickener. As the concentration of the thickener is increased, the gelation temperature will be lowered. An increase of 2% in concentration can cause a 10° C. drop in the gelation temperature for methyl cellulose ether products. A 2% increase in concentration of a solution of hydroxypropyl methyl cellulose ether product lowers the gelation temperature by only 4° C. The degree of substitution of the hydroxypropyl methyl cellulose or the methyl cellulose thickeners will also have an impact on the gelation temperature.

The hydroxypropyl methyl cellulose or the methyl cellulose thickeners may also undergo interfacial gelation, typically at a lower temperature than the bulk gelation discussed above.

As a specific example, a 0.01 wt % solution of Methocel A15 LV cellulose ether (a methyl cellulose ether) exhibits surface gelation at 20° C., whereas bulk gelation with the same product would require a concentration exceeding 12 wt % at such a low temperature. A 0.01 wt % solution of Methocel A15 LV cannot be made to undergo bulk gelation at any temperature. Typically surface gelation will occur rapidly.

Processing Aids

The biofilm disrupting composition may be in solid form, or the composition may be a solution. In the case of a solid mixture of ingredients, the mixture may comprise one or more processing aids such as mannitol, starch, glucose, sucrose etc. in order to allow the composition to be processed into micronized particles, preferably with a mean particle size of less than 500 microns. In a more preferred embodiment, the micronized composition will have a mean particle size of less than 100 microns, and in a particularly preferred embodiment, the micronized composition will have a mean particle size of less than 40 microns. The micronized composition of this particularly preferred embodiment is suitable for inhalation and useful for the disruption and removal of bacterial biofilms found in the lungs in conditions such as cystic fibrosis, bronchitis, chronic obstructive pulmonary disease (COPD), and other airway infections in which biofilms are implicated, such as recurrent rhinosinusitis or pharyngotonsillitis.

EXAMPLES

Example 1

Thermal Gelation Base Gel 1

This example demonstrates the use of the reversible thermal gelation of suitable non-ionic cellulose ether thickeners.

A base solution was prepared by dispersing 2.00 g Methocel A15C (a methyl cellulose ether, with a molecular weight of 1,500 and a degree of substitution if 30%) into a beaker containing 30 ml of deionized water held at 90° C. with stirring. Stirring was continued for a further 20-30 minutes at 90° C. to thoroughly wet the Methocel particles. The beaker was then removed from the hotplate, and 50 ml of cold water added with stirring. The viscosity of the solution was observed to increase as the Methocel fully dissolved. After a further 30-40 minutes of stirring, 5% sodium chloride was then added. The volume of the solution was then adjusted to 100 ml with additional, cold deionized water.

On warming, this base solution underwent a reversible gelation at a temperature of around 32° C. (see Methocel Cellulose Ethers Technical Handbook; Dow Chemicals, September 2002).

Example 2

Thermal Gelation Base 2

A base solution was prepared according to the method of Shirata et al.; "*Body heat responsive gelation of methylcellulose formulation containing betaine*", Bioscience, Biotechnology and Biochemistry (2017), 81, 1829-1836.

A solution of Methylcellulose (Metolose®; Sin-Etsu Chemical Co., Ltd. Tokyo, Japan) was prepared using a dispersion method. 400 mg of the methylcellulose was added to 10 mL of deionized water at approximately 70° C. and stirred for 60 min until evenly dispersed. The solution was cooled to approximately 50° C. by the addition of 10 mL deionized water and the n stirred for 30 min before stirring for 1 h under ice cooling. Glucose (3.0 g), sodium citrate (0.24 g), and trimethylglycine (0.7 g) were added when the solution reached approximately 50° C. Finally the solution was cooled with stirring to 20° C.

Example 3

To 50 ml of the base solution from example 1 is added 5.00 g of L-glutathione (reduced form; Sigma Aldrich), followed by 100 µl of DNAse 1 (recombinant, 10 U/µl; Sigma Aldrich cat. 04716728001). 0.5 g of a 50% solution of benzalkonium chloride is then added. The solution is then stirred to homogenise, and then applied to the wound of a patient.

Example 4

To 50 ml of the base solution from example 1 is added 5.00 g of L-glutathione (reduced form; Sigma Aldrich), followed by 5000 of Spezyme AA (an alpha amylase enzyme solution from Enzyme Solutions, Australia). 0.5 g of a 50% solution of benzalkonium chloride is then added. The solution is then stirred to homogenise, and then applied to the wound of a patient.

Example 5

Inorganic Biocide

A base solution may be prepared by dispersing 2.00 g Methocel A15C (a methyl cellulose ether, with a molecular weight of 1,500 Dalton and a degree of substitution of 30%) into a beaker containing 30 ml of deionized water held at 90° C. with stirring. Stirring is continued for a further 20-30 minutes at 90° C. to thoroughly wet the Methocel particles. The beaker is then removed from the hotplate, and 50 ml of cold water added with stirring. The viscosity of the solution will increase as the Methocel fully dissolved. After a further 30-40 minutes of stirring, 3% sodium chloride is then added, followed by 2% of zinc chloride, 5.0 g glutathione and 1 ml of DNase 1 (10 U/µl).

The volume of the solution is then adjusted to 100 ml with additional, cold deionized water.

Example 6

Surface Gelation Base

A solution of Methocel A15LV (Dow Chemicals) was prepared using a dispersion method. 500 mg of the Methocel is added to 40 mL of deionized water at approximately 80° C. and stirred for 60 min until evenly dispersed. The solution was cooled to approximately 50° C. by the addition of 60 mL deionized water and then stirred for 30 min before stirring for 1 h at 20° C.

Example 7

Example of Unthickened Formulation

To 80 ml of MilliQ water is added 4.79 g sodium chloride, 0.041 g of anhydrous sodium dihydrogen phosphate, 0.238 g of disodium hydrogen phosphate, 0.0030 g ciprofloxacin, 0.92 g of L-glutathione (reduced) and 0.4 ml of Spezyme AA (an amylase solution supplied by Genecore Ltd). The solution is then made up to 100 ml with additional MilliQ water to give an essentially isotonic solution, buffered to pH 7.2. The solution may then be transferred to a spray bottle for topical application to a burn wound bed.

Example 8

Example of Clinical Use 4.78 g of L-glutathione (reduced form; Sigma Aldrich) was placed in a 50 ml Falcon tube, and mixed with 27 g of Povidone Iodine solution. To this was added 1000 of DNase 1 (recombinant, 10 U/μl; Sigma Aldrich cat. 04716728001), followed by 5 ml sterile water. The mixture was then homogenized using a Vortex mixer The composition was then applied to diabetic foot ulcers on two human patients. After application of the paste, the wounds were bandaged and left 2 weeks.

Figure 1:
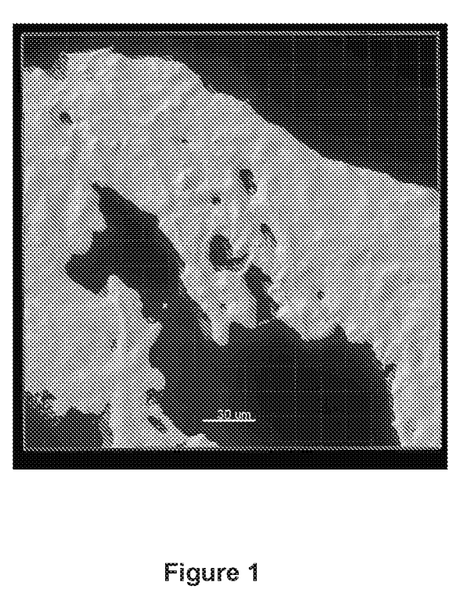
FIG. 1 shows the fluorescence activity observed in a biopsy before the treatment described in Example 8.
Figure 2:
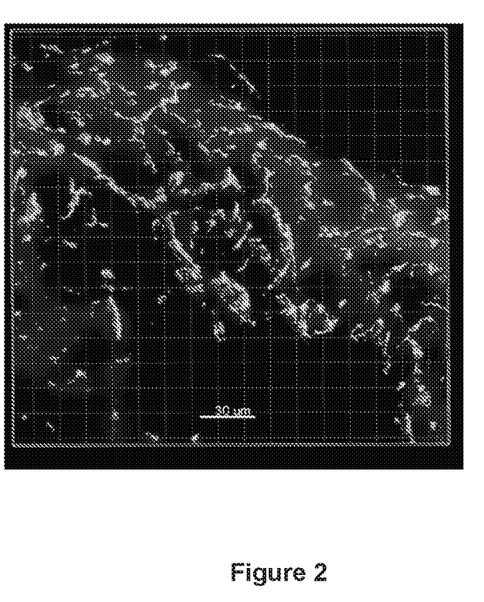
FIG. 2 shows the fluorescence activity observed in a biopsy after the treatment described in Example 8.

Biopsies of the wounds taken before and after treatment were then analysed using fluorescence in situ hybridization using peptide nucleic acid probes (PNA FISH). FIGS. 1 and 2 show fluorescent in-situ hybridisation images of a representative sample area from a patient DFU before treatment (FIG. 1) and after 2 weeks of treatment with the composition on Example 8 (FIG. 2). Treatment showed a >96% reduction in fluorescence intensity ($p<0.05$) between the images of FIG. 1 and FIG. 2.

The invention claimed is:

1. A biofilm disrupting composition comprising:
   (i) at least one biologically acceptable thiol based antioxidant;
   (ii) at least one biofilm disruptor;
   (iii) at least one biocide; and
   (iv) a thickener;
   wherein said composition is a gel and is used for the treatment of chronic wounds.

2. The composition according to claim 1 wherein the biologically acceptable thiol based antioxidant is selected from the group consisting of mercaptoethanol, N-acetyl cysteine, glutathione, thiamphenicol glycinate acetylcysteinate, sodium mercaptoethane sulfonate, lipoic acid and erdosteine.

3. The composition according to claim 2 wherein the biologically acceptable thiol based antioxidant is glutathione.

4. The composition according to claim 1 wherein the biofilm disruptor is at least one enzyme selected from the group consisting of amylase, cellulase, DNase and protease, or mixtures thereof.

5. The composition according to claim 4 wherein the enzyme is DNase.

6. The composition according to claim 1 wherein the biocide is selected from the group consisting of an antibiotic and an antiseptic.

7. The composition according to claim 6 wherein the biocide is a topical antibiotic selected from the group consisting of sulfacetamide sodium, erythromycin, silver sulfadiazine, mupirocin, bacitracin, neomycin, polymyxin, bacitracin, neomycin, polymyxin B and pramoxine.

8. The composition according to claim 6 wherein the antiseptic is selected from the group consisting of cadexomer iodine, povidone iodine, cetrimide, benzalkonium chloride, chlorhexidine gluconate, polyhexanide, hydrogen peroxide, octenidine dihydrochloride, diamidines, silver compounds and zinc salts.

9. The composition according to claim 1 wherein said thickener is selected from the group consisting of methyl cellulose, hydroxypropyl methyl cellulose, hydroxyethyl cellulose, guar, hydroxyethyl guar, xanthan gum, sodium salt of cross linked polyacrylate and hyaluronic acid.

10. The composition according to claim 9 wherein the thickener is methyl cellulose.

11. The composition according to claim 1 further comprising one or more thermal gelation temperature lowering agents selected from the group consisting of sodium chloride, magnesium chloride, iron III chloride, sodium sulfate, aluminium sulfate, sodium carbonate, sodium bicarbonate, sodium citrate, sorbitol, glycerine, trimethylglycine, glucose, maltose and fructose.

12. The composition according to claim 1 further comprising ancillary ingredients selected from the group consisting of secondary surfactants, tonicity modifiers and pH buffers.

13. The composition according to claim 12 wherein the tonicity modifier is selected from the group consisting of inorganic salts and organic tonicity modifiers.

14. The composition according to claim 13 wherein the inorganic salt is selected from the group consisting of sodium bromide, potassium bromide, sodium chloride, potassium chloride, sodium acetate, potassium acetate, sodium citrate, potassium citrate, sodium phosphate and potassium phosphate.

15. The composition according to claim 13 wherein the organic tonicity modifier is selected from the group consisting of propylene glycol, glycerol, mannitol, arabitol, glucose and fructose.

16. A process of preparing a biofilm disrupting composition according to claim 1, which process comprises combining the biologically acceptable thiol based antioxidant, the biofilm disruptor, the biocide, and the thickener, to form said composition, wherein the components, after being combined, form a gel.

17. A method of treating a chronic wound in a patient, comprising administering to said wound a biofilm disrupting composition according to claim 1 in an amount which effectively treats said wound.

18. The method according to claim 17 wherein the chronic wound is a diabetic foot ulcer.

* * * * *